(12) United States Patent
Jacobzon et al.

(10) Patent No.: US 11,696,980 B1
(45) Date of Patent: Jul. 11, 2023

(54) DEVICE AND METHOD FOR PERFUSING A SUBJECT'S HEART VIA THE CORONARY SINUS

(71) Applicants: Yaniv Ben-Haim; SHAARE ZEDEK SCIENTIFIC LTD

(72) Inventors: Ehud Jacobzon, Ness Zionna (IL); Yaniv Ben-Haim, Kfar Mordechai (IL)

(73) Assignee: SHAARE ZEDEK SCIENTIFIC LTD., Jerusalem (IL)

( * ) Notice: Subject to any disclaimer, the term of this patent is extended or adjusted under 35 U.S.C. 154(b) by 0 days.

(21) Appl. No.: 17/834,031

(22) Filed: Jun. 7, 2022

(51) Int. Cl.
| | |
|---|---|
| *A61M 1/36* | (2006.01) |
| *A61M 60/38* | (2021.01) |
| *A61M 60/113* | (2021.01) |
| *A61M 1/14* | (2006.01) |
| *A61M 25/10* | (2013.01) |

(Continued)

(52) U.S. Cl.
CPC ............ *A61M 1/3659* (2014.02); *A61M 1/14* (2013.01); *A61M 1/1698* (2013.01); *A61M 25/1002* (2013.01); *A61M 25/10187* (2013.11); *A61M 60/113* (2021.01); *A61M 60/38* (2021.01); *A61M 2025/0031* (2013.01); *A61M 2025/0037* (2013.01); *A61M 2025/1061* (2013.01); *A61M 2202/0208* (2013.01); *A61M 2205/3331* (2013.01); *A61M 2210/125* (2013.01)

(58) Field of Classification Search
CPC .. A61M 2025/1097; A61M 2025/0039; A61M 2025/1052; A61M 1/1698; A61M 2025/0031; A61M 25/10187; A61M 60/38; A61M 2025/1061; A61M 2025/0037; A61M 2025/0002; A61M 25/1002
See application file for complete search history.

(56) References Cited

U.S. PATENT DOCUMENTS

| | | | | |
|---|---|---|---|---|
| 5,186,713 | A | * | 2/1993 | Raible .................. A61M 25/01 604/6.14 |
| 6,383,172 | B1 | * | 5/2002 | Barbut ................ A61M 1/3659 604/113 |

(Continued)

OTHER PUBLICATIONS

Van de Hoef TP, Nijveldt R, van der Ent M, et al. Pressure-controlled intermittent coronary sinus occlusion (PICSO) in acute ST-segment elevation myocardial infarction: results of the Prepare RAMSES safety and feasibility study. EuroIntervention 2015;11:37-44.

(Continued)

*Primary Examiner* — Leslie R Deak (74) *Attorney, Agent, or Firm* — Pearl Cohen Zedek Latzer Baratz LLP (57) ABSTRACT

A device for perfusing a coronary sinus of a subject's heart which may include: a double-lumen catheter including: a first lumen having: a proximal opening, and a distal opening configured to be positioned in a coronary sinus of a subject's heart; and a second lumen parallel to the first lumen, the second lumen having: a proximal opening, and a distal opening being offset from the distal opening of the first lumen towards the proximal opening of the second lumen in a longitudinal direction, the distal opening of the second lumen being configured to be positioned in a right atrium of the subject's heart; and an oxygenator connected to the proximal openings of the first lumen and the second lumen, the oxygenator is configured to oxygenate deoxygenated blood.

15 Claims, 4 Drawing Sheets

(51) Int. Cl.
*A61M 1/16* (2006.01)
*A61M 25/00* (2006.01)

(56) References Cited

U.S. PATENT DOCUMENTS

| | | | | |
|---|---|---|---|---|
| 6,435,189 | B1* | 8/2002 | Lewis | A61M 25/0032 604/4.01 |
| 6,866,650 | B2* | 3/2005 | Stevens | A61M 25/0041 604/102.01 |
| 2006/0195060 | A1* | 8/2006 | Navia | A61F 2/90 604/96.01 |
| 2011/0295177 | A1* | 12/2011 | Mohl | A61M 60/32 604/509 |
| 2012/0302995 | A1* | 11/2012 | Hochareon | A61M 1/3604 604/113 |
| 2018/0078698 | A1* | 3/2018 | Olaf | A61M 1/3667 |

OTHER PUBLICATIONS

Banai S, Ben Muvhar S, Parikh KH, et al. Coronary sinus reducer stent for the treatment of chronic refractory angina pectoris: a prospective, open-label, multicenter, safety feasibility first-in-man study. J Am Coll Cardiol 2007;49:1783-9.

Becks CS, Stanton E, Batiuchok W, et al. Revascularization of the heart by graft of systemic artery into coronary sinus. J Am Med Assoc 1948;137:436-42.

Hochberg MS, Roberts WC, Morrow AG, et al. Selective arterialization of the coronary venous system. Encouraging long-term flow evaluation utilizing radioactive microspheres. J Thorac Cardiovasc Surg 1979;77:1-12.

Mohl W. Coronary sinus interventions: from concept to clinics. J Card Surg—2:467;1987.93.

Meerbaum S, Lang TW, Osher JV, et al. Diastolic retroperfusion of acutely ischemic myocardium. Am J Cardiol 1976;37:588-98.

O'Byrne GT, Nienaber CA, Miyazaki A, et al. Positron emission tomography demonstrates that coronary sinus retroperfusion can restore regional myocardial perfusion and preserve metabolism. J Am Coll Cardiol 1991;18: 70-257.

Pressure monitoring of the coronary sinus during retrograde cardioplegia. T Higami, K Ogawa, N Mukohara, m Nishiwaki. Nihon Kyobu Geka Gakkai Zasshi. Jun. 1991; 39(6): 848-54.

Optimal flow rates for retrograde warm cardioplegia. J S Ikonomidis, T M Yau, L Tumiati, et al. J Thorac Cardiovasc Surg. Feb. 1994; 107(2): 510-9.

Retrograde coronary venous perfusion at low pressure; M.F. Toscano, M.D et al. vol 7, No. 1, Mar. 1980.

Reconsidering the back door approach by targeting the coronary sinus in ischaemic heart disease; Giovanni Luigi De Maria et al.; published Jun. 10, 2016.

* cited by examiner

DEVICE AND METHOD FOR PERFUSING A SUBJECT'S HEART VIA THE CORONARY SINUS

FIELD OF THE INVENTION

The present invention relates to the field of treatment of myocardial ischemia and coronary artery disease, and more particularly, to device and method for perfusing a subject's heart via coronary sinus venous system.

BACKGROUND OF THE INVENTION

Acute myocardial infarction occurs when blood flow to a coronary artery of a subject's heart decreases or stops, e.g. due to a narrowing of the coronary artery, thrombus, or plaque rupture. In order to treat the narrowing of the coronary artery, the subject undergoes a percutaneous coronary intervention procedure at a catheterization laboratory, in which a balloon is inflated, and a stent is inserted into a narrowed or occluded point of the coronary artery in order to resume or increase blood flow. The treatment of the myocardial infarction is time critical and needs to be performed within 60-90 minutes from contact of the subject with a medical provider. However, in some cases, e.g. due to complex coronary anatomy or high-risk coronary lesion, it might take more time to overcome the critical obstruction and to resume or increase flow. A delay in treatment may cause or prolong myocardial ischemia, irreversible cardiac muscle damage, and in some cases cause life threatening cardiogenic shock. The prior art has not provided a simple device and method that may perfuse the subject's heart in complex or high-risk situations and provide the cardiologists with the time required to perform the optimal treatment for the patient.

SUMMARY OF THE INVENTION

Embodiments of the present invention may provide a device for perfusing a coronary sinus of a subject's heart, which may include: a double-lumen catheter including: a first lumen having: a proximal opening, and a distal opening configured to be positioned in a coronary sinus of a subject's heart; and a second lumen parallel to the first lumen, the second lumen having: a proximal opening, and a distal opening being offset from the distal opening of the first lumen towards the proximal opening of the second lumen in a longitudinal direction, the distal opening of the second lumen being configured to be positioned in a right atrium of the subject's heart; and an oxygenator connected to the proximal openings of the first lumen and the second lumen, the oxygenator is configured to oxygenate deoxygenated blood. The distal opening of the second lumen may be offset from the distal opening of the first lumen by 4-8 cm. The device may include a pump to drive the deoxygenated blood from the right atrium to the oxygenator through the second lumen of the catheter and to drive the oxygenated blood from the oxygenator to the coronary sinus through the first lumen of the catheter. The device may include an inflatable member positioned on an outer portion of the catheter in a region between the distal opening of the first lumen and the distal opening of the second lumen. The inflatable member may be offset from the distal opening of the first lumen by 1-3 cm. The device may include a conduit configured to deliver a pressurized fluid to the inflatable member to alternately inflate and deflate the inflatable member. The inflatable member may have a transverse shape that occupies a portion of a transverse cross-section of the coronary sinus when the inflatable member is inflated in the coronary sinus. The device may include a pressure sensor positioned on the outer portion of the catheter in a region between the distal opening of the first lumen and the inflatable member. The pressure sensor may measure a pressure in the coronary sinus. The measure of inflation of the inflatable member is determined based on signals from the pressure sensor to control the pressure in the coronary sinus. The inflatable member may fixate the catheter in the coronary sinus when the inflatable member is inflated in the coronary sinus. The inflatable member may limit a flow of blood from the coronary sinus to the right atrium of the subject's heart when the inflatable member is inflated in the coronary sinus.

Embodiments of the present invention may provide a method of perfusing a coronary sinus of a subject's heart, which may include: providing a double-lumen catheter, the catheter including: a first lumen and a second lumen being parallel to each other, wherein a distal opening of the second lumen is offset from a distal opening of the first lumen towards a proximal opening of the second lumen in a longitudinal direction; inserting the catheter into a subject's heart to position the distal opening of the first lumen in a coronary sinus of the subject's heart and position the distal opening of the second lumen in a right atrium of the subject's heart; with a pump, driving deoxygenated blood from the right atrium through the second lumen of the catheter; with an oxygenator, oxygenating the deoxygenated blood; and with the pump, driving the oxygenated blood to the coronary sinus through the first lumen of the catheter. The catheter may be fixated within the coronary sinus with an inflatable member positioned on an outer portion of the catheter in a region between the distal opening of the first lumen and the distal opening of the second lumen. The measure of inflation of the inflatable member may control a pressure in the coronary sinus. The pressure in the coronary sinus may be measured with a pressure sensor positioned on the outer portion of the catheter in a region between the distal opening of the first lumen and inflatable member. The measure of inflation of the inflatable member may be controlled based on signals from the pressure sensor. The inflatable member may be deflated, and the catheter may be removed from the subject's heart.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings.

It will be appreciated that, for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Embodiments of the present invention provide a device for perfusing a subject's heart via a coronary sinus. The coronary sinus is a collection of veins joined together to form a large vessel that returns deoxygenated blood from the heart muscle to the right side of the heart so that it can be replenished with oxygen. The device may include a double-lumen catheter including a first lumen and a second lumen being parallel to each other, wherein a distal opening of the second lumen is offset from a distal opening of the first lumen towards a proximal opening of the second lumen in a longitudinal direction. The catheter is configured such that when the catheter is inserted into the subject's heart, the distal opening of the first lumen in positioned in the coronary sinus of the subject's heart and the distal opening of the second lumen is positioned in a right atrium of the subject's heart. The device may include an oxygenator to oxygenate deoxygenated (e.g. venous) blood. The oxygenator may be connected to the proximal openings of the first lumen and the second lumen. The device may include a pump (which may be, e.g. part of the oxygenator) to drive deoxygenated blood from the right atrium of the subject's heart through the second lumen of the catheter and to drive the oxygenated blood to the coronary sinus through the first lumen of the catheter. The device may include an inflatable member positioned on an outer portion of the catheter in a region between the distal opening of the first lumen and the distal opening of the second lumen. When inflated, the inflatable member may fixate the catheter within the coronary sinus. When inflated, the inflatable member may occlude a portion of a transverse cross-section of the coronary sinus to ensure that blood can flow between the coronary sinus and the right atrium and of the subject's heart. The measure of inflation of the inflatable member may be determined to control a measure of occlusion of the transverse cross-section of the coronary sinus by the inflatable member. The measure of inflation of the inflatable member and/or the flowrate of the oxygenated blood to the coronary sinus may be determined to control a pressure in the coronary sinus of the subject's heart. Operation of the device is simple and can be easily performed by the cardiologist in the case of complex or high-risk situations of myocardial infarction that delay the percutaneous coronary intervention procedure. Perfusing the subject's heart via the coronary sinus using the device may provide the cardiologist with a time to select and perform the optimal treatment for the myocardial infarction while eliminating (or at least reducing) a risk of causing prolonged myocardial ischemia, irreversible cardiac muscle damage and/or cardiogenic shock.

Figure 1A:
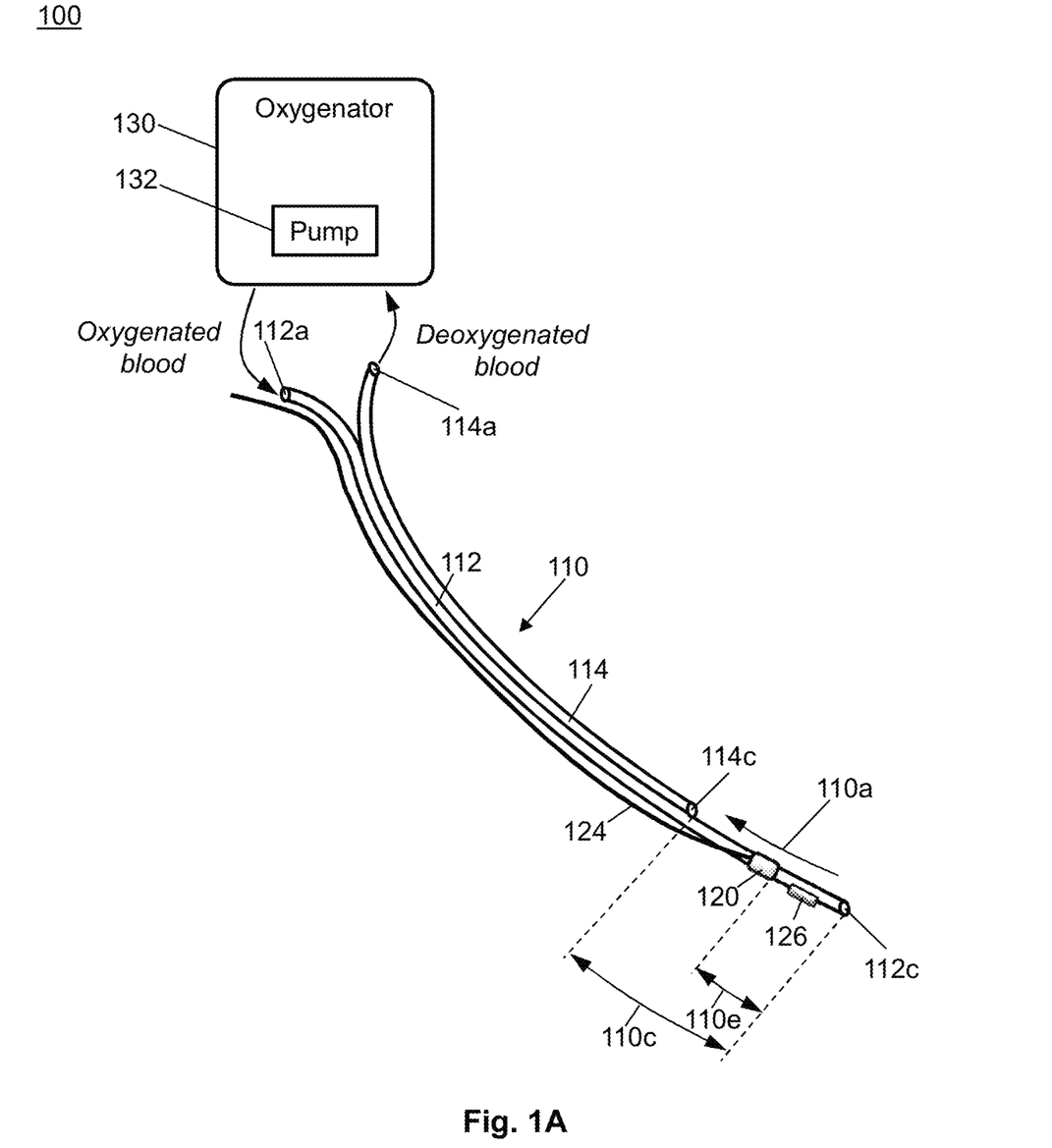
FIGS. 1A and 1B are schematic illustrations of a device for perfusing a subject's heart via a coronary sinus, according to some embodiments of the invention.
Figure 1B:
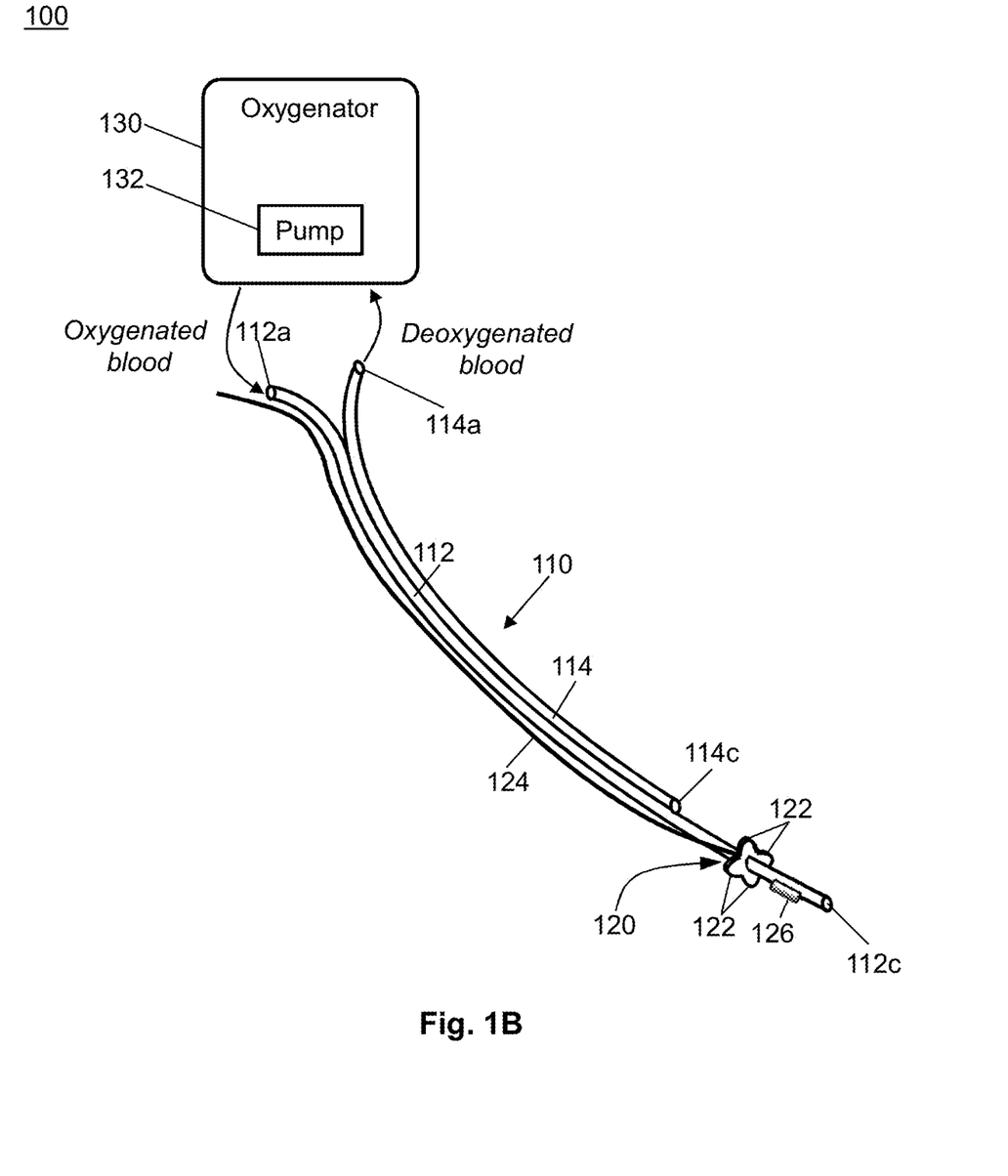

Reference is now made to FIGS. 1A and 1B, which are schematic illustrations of a device 100 for perfusing a subject's heart via a coronary sinus, according to some embodiments of the invention.

Device 100 may include a catheter 110. Catheter 110 may be a double-lumen catheter. Catheter 110 may include a first lumen 112 and a second lumen 114. First lumen 112 and second lumen 114 may be parallel to each other along at least a portion of their lengths.

First lumen 112 of catheter 110 may have a proximal opening 112a and a distal opening 112c. Second lumen 114 of catheter 110 may have a proximal opening 114a and a distal opening 114c. Distal opening 114c of second lumen 114 may be offset or distanced from distal opening 112c of first lumen 112 towards proximal opening 114a of second lumen 114 in a longitudinal direction 110a of catheter 110. For example, distal opening 114c of second lumen 114 may be offset or distanced from distal opening 112c of first lumen 112 by 4-8 cm, e.g. by 5 cm. The length of first lumen 112 may be in a range of, for example, 50-70 cm, e.g. 60 cm. The length of second lumen 114 may be, for example, in a range of 40-60 cm, e.g. 55 cm. The dimensions may, for example, allow insertion of catheter 110 into the subject's heart through, e.g. right internal jugular vein at the subject's neck, positioning of distal opening 112c of first lumen 112 in the coronary sinus of the subject's heart, positioning of distal opening 114c of second lumen 114 in the right atrium of the subject's heart, and further allow manipulation and connection of catheter 110 to an oxygenator 130 (e.g. as described below).

Device 100 may include an inflatable (e.g. expandable) member (e.g. an inflatable balloon) 120. FIGS. 1A and 1B show inflated member 120 in its deflated and inflated states, respectively. Inflatable member 120 may be positioned on or connected to an outer portion of catheter 110, e.g. in a region 110c between distal opening 112c of first lumen 112 and distal opening 114c of second lumen 114 of catheter 110. For example, inflatable member 120 may be offset or distanced from distal opening 112c of first lumen 112 by 1-3 cm, e.g. by 2 cm. Device 100 may include a conduit 124 to deliver a pressurized fluid to and from inflatable member 120 to alternately inflate or deflate inflatable member 120. When inflated, inflatable member 120 may have a transverse shape that occludes a portion of a transverse cross-section of the coronary sinus of the subject's heart (e.g. a portion less than the entire cross section). Inflatable member 120 may have a transverse shape that prevents inflatable member 120 from occluding the entire transverse cross-section of the coronary sinus of the subject's heart when inflatable member 120 is inflated in the coronary sinus. When inflated, inflatable member 120 may have, for example, a non-circular transverse shape. For example, when inflated, inflatable member 120 may have four lobes 122 radially protruding outward from catheter 110 (e.g. as shown in FIG. 1B). Other examples of the transverse shape of inflatable member 120 in its inflated state may include triangular or quadrilateral (e.g. rhombus) shapes. Inflatable member 120 may have other transverse shapes as well.

Device 100 may include a pressure sensor 126. Pressure sensor 126 may be positioned on or connected to the outer portion of catheter 110, e.g. in a region 110e between distal opening 112c of first lumen 110 and inflatable member 120. Pressure sensor 126 may measure a pressure in the coronary sinus of the subject's heart.

Device 100 may include an oxygenator 130. Oxygenator 130 may be connected to proximal openings 112a, 114a of first lumen 112 and second lumen 114, respectively (e.g. as schematically indicated by arrowed arcs in FIGS. 1A and 1B). Oxygenator 130 may include a pump 132. Oxygenator 130 may receive deoxygenated (e.g. venous) blood. Oxygenator 130 may oxygenate the deoxygenated blood.

Figure 2:
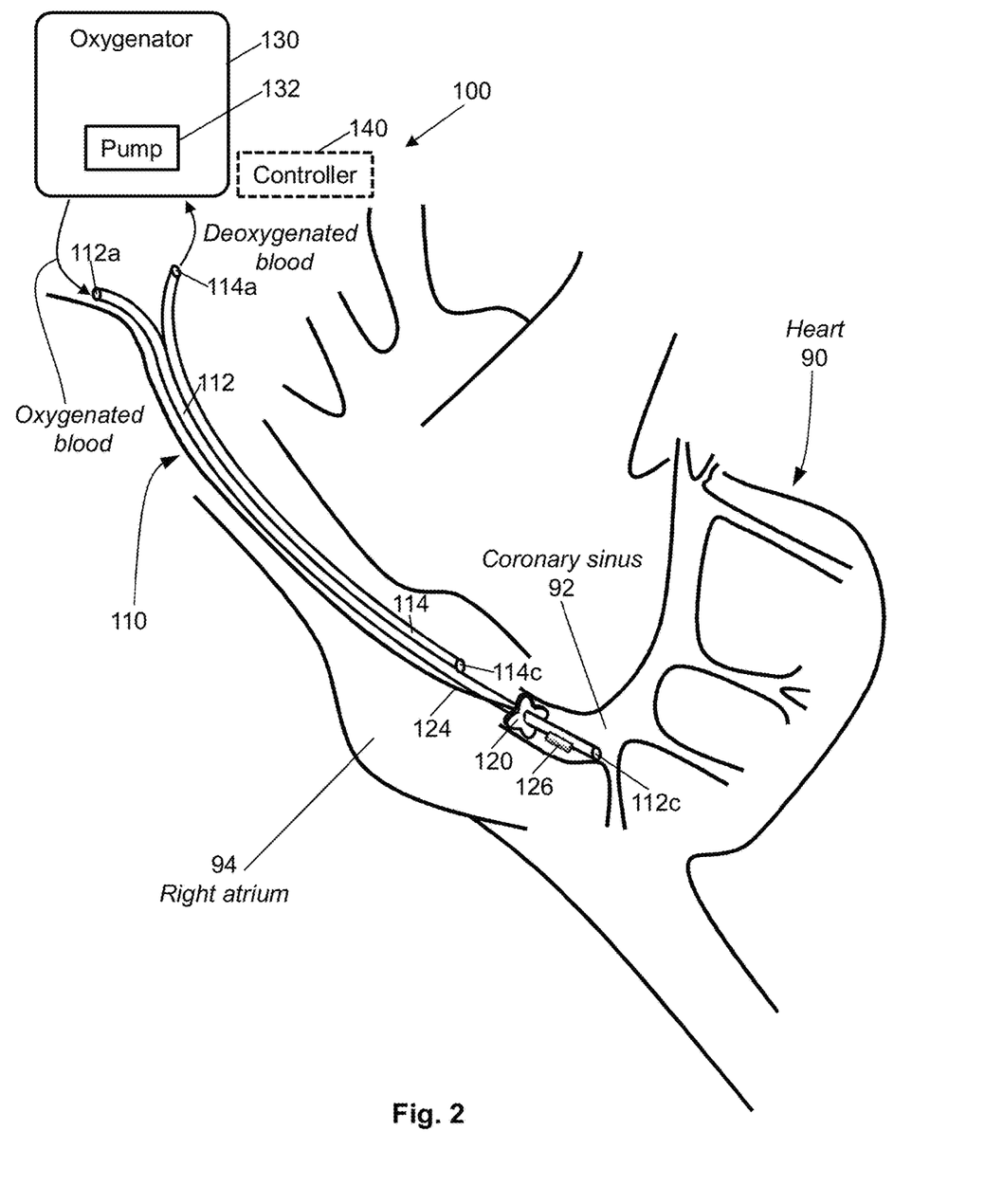
FIG. 2 is a schematic illustration of a subject's heart and of the device for perfusing the subject's heart via the coronary sinus, according to some embodiments of the invention.

Reference is now made to FIG. 2, which is a schematic illustration of a subject's heart 90 and of device 100 for perfusing subject's heart 90 via coronary sinus 92, according to some embodiments of the invention.

As schematically shown in FIG. 2, coronary sinus 92 is a collection of myocardial veins joined together to form a large vessel that returns deoxygenated blood from the heart muscle to right atrium 94 of heart 90 so that the blood can be replenished with oxygen.

In operation, catheter 110 of device 100 may be inserted into subject's heart 90, e.g. via the right internal jugular vein or any other suitable blood vessel known in the art, to position distal opening 112c of first lumen 112 within coronary sinus 92 and to position distal opening 114c of second lumen 114 in a right atrium 94 of subject's heart 90. A pressurized fluid may be delivered to inflatable member 120 through conduit 124 to inflate inflatable member 120. When inflated, inflatable member 120 may fixate catheter 110 within coronary sinus 92 (e.g. as shown in FIG. 2). When inflated, the transverse shape of inflatable member 120 occludes only a portion of the transverse cross-section of coronary sinus 92 (e.g. as shown in FIG. 2) thus ensuring that blood can flow between coronary sinus 92 and right antrum 94 of subject's heart 90.

Device 100 is configured such that once catheter 110 is positioned in subject's heart 90 (e.g. as described above and schematically shown in FIG. 2), pump 132 may drive deoxygenated (e.g. venous) blood from right atrium 94 of subject's heart 90 through second lumen 114 of catheter 110 to oxygenator 130. Oxygenator 130 may receive the deoxygenated blood from second lumen 114 of catheter 110 and oxygenate the deoxygenated blood. Pump 132 may drive the oxygenated blood from oxygenator 130 to coronary sinus 92 of subject's heart 90 through first lumen 112 of catheter 110. The oxygenated blood received within coronary sinus 92 may perfuse subject's heart 90 by transporting oxygen into the tissue of subject's heart 90.

The measure of inflation of inflatable member 120 and/or the flowrate of the oxygenated blood to coronary sinus 92 through first lumen 112 may be determined to control a pressure in coronary sinus 92 of subject's heart 90. For example, pressure sensor 126 may measure the pressure within coronary sinus 92 and the measure of inflation of inflatable member 120 and/or the flowrate of the oxygenated blood to coronary sinus 92 may be determined based on that measured pressure. For example, too high pressure (e.g. a pressure above a specified threshold value) in coronary sinus 92 may indicate that inflatable member 120 is over inflated and occludes a too large portion of the transverse cross-section of coronary sinus 92 thus over-limiting the blood flow between coronary sinus 92 and right atrium 94. In this case, inflatable member 120 may be deflated by removing pressurized fluid from inflatable member 120 through conduit 124 until the pressure in coronary sinus 92 measured by pressure sensor 126 reaches a desired pressure value. The control of inflation and deflation of inflatable member 120 and/or the flowrate of the oxygenated blood to coronary sinus 92 based on signals from pressure sensor 126 may be made by, for example, a cardiologist performing the procedure. In various embodiments, device 100 may include a controller 140 (e.g. indicated in FIG. 2 by dashed rectangle) that may, based on signals from pressure sensor 126, control delivery of the pressurized fluid to and from inflatable member 120 and/or control the flowrate of the oxygenated blood to coronary sinus 92.

Inflated inflatable member 120 may limit the blood flow between coronary sinus 92 and right atrium 94 of subject's heart 90 thus ensuring that the oxygenated blood remains within coronary sinus 92 for a long enough time (e.g. or at least for longer than in a case without inflatable member 120) to enhance the perfusion effect. Other devices such as, e.g. a reducer stent, may be used instead of or in addition to inflatable member 120, configured to reduce or limit the blood flow between coronary sinus 92 and right atrium 94 of subject's heart 90 during the procedure.

Insertion and operation of device 100 is simple and can be easily performed by the cardiologist in the case of complex or high-risk situations of myocardial infarction that delay the percutaneous coronary intervention procedure. Perfusing subject's heart 90 via coronary sinus 92 using device 100 may provide the cardiologist with a time to select and perform the optimal treatment for the myocardial infarction while eliminating (or at least reducing) a risk of causing prolonged myocardial ischemia, cardiac muscle damage and/or cardiogenic shock.

Once the procedure (e.g. myocardial infarction treatment) is complete, inflatable member 120 may be deflated and catheter 110 may be removed from subject's heart 90.

Figure 3:
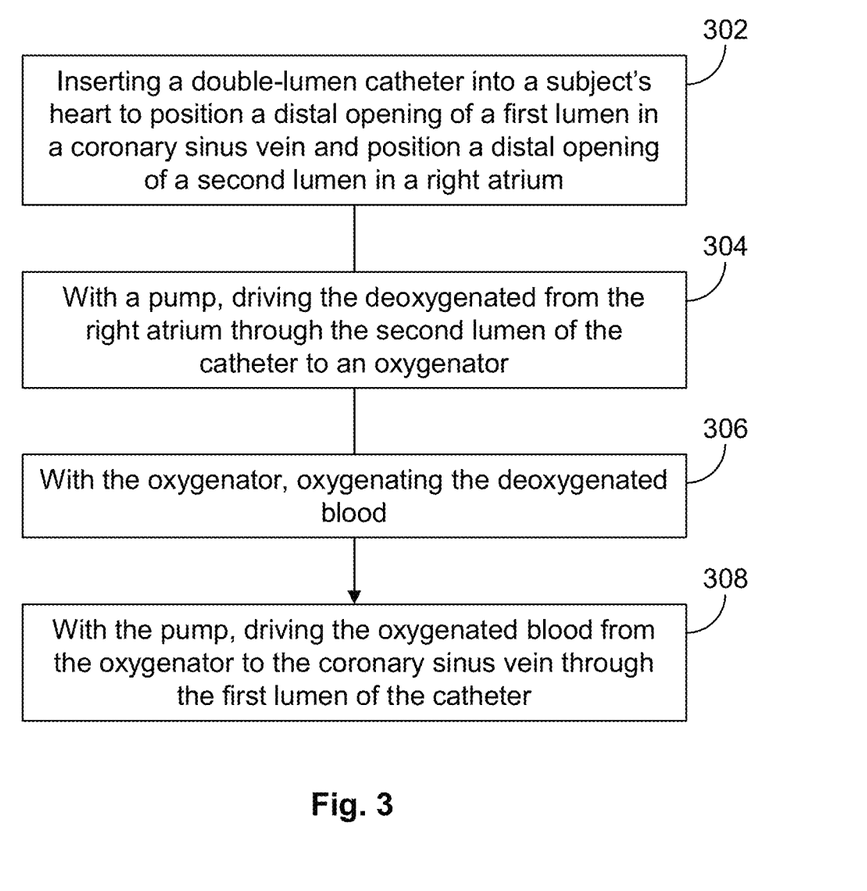
FIG. 3 is a flowchart of a method of perfusing a subject's heart via a coronary sinus, according to some embodiments of the invention.

Reference is now made to FIG. 3, which is a flowchart of a method of perfusing a subject's heart via a coronary sinus, according to some embodiments of the invention.

The operations of FIG. 3 may be performed with the equipment shown in FIGS. 1A-1B, 2 but may be performed with other equipment.

In operation 302, a double-lumen catheter may be inserted into the subject's heart to position a distal opening of a first lumen of the catheter in the coronary sinus of the subject's heart and position a distal opening of a second lumen of the catheter in the right atrium of the subject's heart (e.g. as described above with respect to FIG. 2). For example, the catheter may be catheter 110 described above with respect to FIGS. 1A-1B, 2. As described above with respect to FIGS. 1A-1B, 2, catheter 110 may include first lumen 112 and second lumen 114 being parallel to each other, wherein a distal opening 114c of second lumen 114 is offset or distanced from a distal opening 112c of first lumen 112 towards a proximal opening 114a of second lumen 114 in longitudinal direction 110a of catheter 110. Insertion of the catheter into the subject's heart is simple and can be easily performed by the cardiologist (e.g. as described above with respect to FIG. 2).

In operation 304, the deoxygenated (e.g. venous) blood may be driven by a pump (e.g. pump 132 described above with respect to FIGS. 1A-1B, 2) from the right atrium of the subject's heart through the second lumen of the catheter to an oxygenator (e.g. oxygenator 130 described above with respect to FIGS. 1A-1B, 2). In operation 306, the deoxygenated blood may be oxygenated with the oxygenator (e.g. as described above with respect to FIGS. 1A-1B, 2). In operation 308, the oxygenated blood may be driven by the pump from the oxygenator to the coronary sinus of the subject's heart through the first lumen of the catheter (e.g. as described above with respect to FIGS. 1A-1B, 2).

The catheter may include an inflatable member (e.g. inflatable member 120 described above with respect to FIGS. 1A-1B, 2) positioned on or connected to an outer portion of the catheter in a region between the distal opening of the first lumen and the distal opening of the second lumen. In operation, the inflatable member may be inflated to fixate the catheter within the coronary sinus. The measure of inflation of the inflatable member may be controlled to control the pressure within the coronary sinus (e.g. as described above with respect to FIG. 2). The pressure within the coronary sinus may be measured by a pressure sensor (e.g. pressure sensor 126 described above with respect to FIGS. 1A-1B, 2). The inflation and deflation of the inflatable member may be controlled based on signals from the pressure sensor. For example, the inflation and deflation of the inflatable member may be controlled by the cardiologist and/or by a controller (e.g. controller 140 described above with respect to FIG. 2).

Once the procedure is complete, the inflatable member may be deflated, and the catheter may be removed from the subject's heart.

The operations described with respect to FIG. 3 are simple and can be easily performed by the cardiologist in the case of complex or high-risk situations of myocardial infarction that delay the percutaneous coronary intervention procedure. Perfusing the subject's heart via the coronary sinus as described with respect to FIG. 3 may provide the cardiologist with a time to select and perform the optimal treatment for the myocardial infarction while eliminating (or at least reducing) a risk of causing prolong myocardial ischemia, cardiac muscle damage and/or cardiogenic shock of the subject's heart.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A device for perfusing a coronary sinus of a subject's heart, the device comprising:
   a double-lumen catheter comprising:
      a first lumen having:
         a proximal opening, and
         a distal opening configured to be positioned in a coronary sinus of a subject's heart;
      a second lumen parallel to the first lumen, the second lumen having:
         a proximal opening, and
         a distal opening being offset from the distal opening of the first lumen towards the proximal opening of the second lumen in a longitudinal direction, the distal opening of the second lumen being configured to be positioned in a right atrium of the subject's heart; and
      an inflatable member positioned on an outer portion of the catheter in a region between the distal opening of the first lumen and the distal opening of the second lumen;
         wherein the inflatable member has a shape configured to occlude a portion less than an entire transverse cross-section of the coronary sinus to ensure a flow of blood between the coronary sinus and the right atrium when the inflatable member is completely inflated in the coronary sinus, the shape of the inflatable member being also configured to fixate the catheter in the coronary sinus when the inflatable member is completely inflated in the coronary sinus; and
   an oxygenator connected to the proximal openings of the first lumen and the second lumen, the oxygenator is configured to oxygenate deoxygenated blood.

2. The device of claim 1, wherein the distal opening of the second lumen is offset from the distal opening of the first lumen by 4-8 cm to ensure positioning of the distal opening of the second lumen in the right atrium of the subject's heart when the distal opening of the first lumen is positioned in the coronary sinus of the subject's heart.

3. The device of claim 1, comprising a pump to drive the deoxygenated blood from the right atrium to the oxygenator through the second lumen of the catheter and to drive the oxygenated blood from the oxygenator to the coronary sinus through the first lumen of the catheter.

4. The device of claim 1, wherein the inflatable member is offset from the distal opening of the first lumen by 1-3 cm.

5. The device of claim 1, comprising a conduit configured to deliver a pressurized fluid to the inflatable member to alternately inflate and deflate the inflatable member.

6. The device of claim 1, comprising a pressure sensor positioned on the outer portion of the catheter in a region between the distal opening of the first lumen and the inflatable member, the pressure sensor is to measure a pressure in the coronary sinus.

7. The device of claim 6, wherein a measure of inflation of the inflatable member is determined based on signals from the pressure sensor to control the pressure in the coronary sinus.

8. The device of claim 1, wherein the inflatable member fixates the catheter in the coronary sinus when the inflatable member is inflated in the coronary sinus.

9. The device of claim 1, wherein the inflatable member limits a flow of blood from the coronary sinus to the right atrium of the subject's heart when the inflatable member is inflated in the coronary sinus.

10. A method of perfusing a coronary sinus of a subject's heart, the method comprising:
providing a double-lumen catheter, the catheter comprising:
a first lumen and a second lumen being parallel to each other, wherein a distal opening of the second lumen is offset from a distal opening of the first lumen towards a proximal opening of the second lumen by a distance of 4-8 cm in a longitudinal direction;
inserting the catheter into a subject's heart to position the distal opening of the first lumen in a coronary sinus of the subject's heart and position the distal opening of the second lumen in a right atrium of the subject's heart;
with a pump, driving deoxygenated blood from the right atrium through the second lumen of the catheter;
with an oxygenator, oxygenating the deoxygenated blood; and
with the pump, driving the oxygenated blood to the coronary sinus through the first lumen of the catheter.

11. The method of claim 10, comprising: with an inflatable member positioned on an outer portion of the catheter in a region between the distal opening of the first lumen and the distal opening of the second lumen, fixating the catheter within the coronary sinus.

12. The method of claim 10, comprising: with an inflatable member positioned on an outer portion of the catheter in a region between the distal opening of the first lumen and the distal opening of the second lumen, controlling a measure of inflation of the inflatable member to control a pressure in the coronary sinus.

13. The method of claim 12, comprising: with a pressure sensor positioned on the outer portion of the catheter in a region between the distal opening of the first lumen and inflatable member, measuring the pressure in the coronary sinus.

14. The method of claim 13, comprising: based on signals from the pressure sensor, controlling the measure of inflation of the inflatable member.

15. The method of claim 10, further comprising:
deflating the inflatable member; and
removing the catheter from the subject's heart.

* * * * *